US00PP22176P2

(12) United States Plant Patent
Wood

(10) Patent No.: US PP22,176 P2
(45) Date of Patent: Oct. 4, 2011

(54) ***POTENTILLA* PLANT NAMED 'LUNDY'**

(50) Latin Name: *Potentilla fruticosa*
Varietal Denomination: Lundy

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/807,830

(22) Filed: Sep. 14, 2010

(51) Int. Cl.
*A01H 5/00* (2006.01)

(52) U.S. Cl. ..... Plt./237

(58) Field of Classification Search ..... Plt./237
See application file for complete search history.

*Primary Examiner* — Kent L Bell
(74) *Attorney, Agent, or Firm* — C. A. Whealy

(57) ABSTRACT

A new and distinct cultivar of *Potentilla* plant named 'Lundy', characterized by its compact, upright and outwardly spreading plant habit; freely branching habit, dense and bushy plant form; dark green-colored leaves; large dark yellow-colored flowers; long flowering period; and good garden performance.

2 Drawing Sheets

Botanical designation: *Potentilla fruticosa*.
Cultivar denomination: 'LUNDY'.

BACKGROUND OF THE INVENTION

The present invention relates to a new and distinct cultivar of *Potentilla* plant, botanically known as *Potentilla fruticosa* and hereinafter referred to by the name 'Lundy'.

The new *Potentilla* plant is a product of a planned breeding program conducted by the Inventor in Grand Haven, Mich. The objective of the breeding program was to develop new uniform *Potentilla* plants with attractive flower color.

The new *Potentilla* plant originated from an open-pollination during the summer of 1999 of *Potentilla fruticosa* 'Hopley's Orange', not patented, as the female, or seed, parent with an unknown selection of *Potentilla fruticosa* as the male, or pollen, parent. The new *Potentilla* plant was discovered and selected by the Inventor during the summer of 2006 as a flowering plant within the progeny of the stated open-pollination in a controlled environment in Grand Haven, Mich.

Asexual reproduction of the new *Potentilla* plant by softwood cuttings in a controlled environment in Grand Haven, Mich. since July, 2006, has shown that the unique features of this new *Potentilla* plant are stable and reproduced true to type in successive generations.

SUMMARY OF THE INVENTION

Plants of the new *Potentilla* have been observed under all possible cultural and environmental conditions. The phenotype may vary somewhat with variations in cultural practices and environment such as temperature and light intensity without, however, any variance in genotype.

The following traits have been repeatedly observed and are determined to be the unique characteristics of 'Lundy'. These characteristics in combination distinguish 'Lundy' as a new and distinct *Potentilla* plant:

1. Compact, upright and outwardly spreading plant habit.
2. Freely branching habit, dense and bushy plant form.
3. Dark green-colored leaves.
4. Large dark yellow-colored flowers.
5. Long flowering period.
6. Good garden performance.

Plants of the new *Potentilla* can be compared to plants of the parent, 'Hopley's Orange'. Plants of the new *Potentilla* differ primarily from plants of 'Hopley's Orange' in the following characteristics:

1. Plants of the new *Potentilla* have larger flowers than plants of 'Hopley's Orange'.
2. Plants of the new *Potentilla* and 'Hopley's Orange' differ in flower color as plants of 'Hopley's Orange' have orange-colored flowers.

Plants of the new *Potentilla* can be compared to plants of the *Potentilla* 'Goldfinger', not patented. In side-by-side comparisons, plants of the new *Potentilla* differ primarily from plants of 'Goldfinger' in the following characteristics:

1. Plants of the new *Potentilla* are more compact than plants of 'Goldfinger'.
2. Plants of the new *Potentilla* have darker green-colored leaves than plants of 'Goldfinger'.
3. Plants of the new *Potentilla* have larger flowers than plants of 'Goldfinger'.

Plants of the new *Potentilla* can also be compared to plants of the *Potentilla* 'Fargo', not patented. In side-by-side comparisons, plants of the new *Potentilla* differ primarily from plants of 'Fargo' in the following characteristics:

1. Plants of the new *Potentilla* have darker green-colored leaves than plants of 'Fargo'.
2. Plants of the new *Potentilla* have larger flowers than plants of 'Fargo'.

BRIEF DESCRIPTION OF THE PHOTOGRAPHS

The accompanying colored photographs illustrate the overall appearance of the new *Potentilla* plant showing the colors as true as it is reasonably possible to obtain in colored reproductions of this type.

Colors in the photographs may differ slightly from the color values cited in the detailed botanical description which accurately describe the colors of the new *Potentilla* plant.

The photograph on the first sheet comprises a side perspective view of typical flowering plants of 'Lundy' grown in an outdoor nursery.

The photograph on the second sheet is a close-up view of a typical flowering plant of 'Lundy'.

DETAILED BOTANICAL DESCRIPTION

The aforementioned photographs and following observations, measurements and values describe plants grown during the spring and summer in an outdoor nursery in Grand Haven, Mich. and under conditions which closely approximate commercial *Potentilla* production. Plants were four years old when the photographs and the description were taken. In the description, color references are made to The Royal Horticultural Society Colour Chart, 2001 Edition, except where general terms of ordinary dictionary significance are used.

Botanical classification: *Potentilla fruticosa* 'Lundy'.

Parentage:

*Female, or seed, parent.*—*Potentilla fruticosa* 'Hopley's Orange', not patented.

*Male, or pollen, parent.*—Unknown selection of *Potentilla fruticosa*, not patented.

Propagation:

*Type.*—By softwood cuttings.

*Time to initiate roots, summer.*—About 18 days at 27° C.

*Time to produce a rooted young plant, summer.*—About three months at 27° C.

*Root description.*—Fine and thick, fibrous.

*Rooting habit.*—Freely branching, dense.

Plant description:

*Plant form and growth habit.*—Perennial deciduous shrub; compact, upright and outwardly spreading plant habit; plants rounded and low mounding; freely branching habit with numerous lateral branches developing per plant, dense and bushy plant form; vigorous growth habit.

*Plant height.*—About 55 cm.

*Plant diameter* (*area of spread*).—About 70 cm.

Lateral branch description:

*Length.*—About 9 cm.

*Diameter.*—About 1.5 cm.

*Internode length.*—About 1.5 cm.

*Strength.*—Strong.

*Texture.*—Slightly pubescent; woody with development.

*Color, developing.*—Close to 144D.

*Color, woody.*—Close to 199A.

Foliage description:

*Arrangement.*—Alternate; palmately compound with five leaflets per leaf.

*Leaflet length.*—About 1.6 cm.

*Leaflet width.*—About 5 mm.

*Leaflet shape.*—Oblong to lanceolate.

*Leaflet apex.*—Obtuse.

*Leaflet base.*—Cuneate to obtuse.

*Leaflet margin.*—Entire.

*Leaflet texture, upper surface.*—Smooth, glabrous.

*Leaflet texture, lower surface.*—Sparsely pubescent.

*Leaflet venation pattern.*—Pinnate, reticulate.

*Leaflet color.*—Developing leaves, upper surface: Close to 137A. Developing leaves, lower surface: Close to 138B. Mature leaves, upper surface: Close to 137A; venation, close to 137A. Mature leaves, lower surface: Close to 138B; venation, close to 138B.

*Leaflet petiole.*—Length: About 3 mm to 4 mm. Diameter: Less than 1 mm. Texture, upper and lower surfaces: Smooth, glabrous. Color, upper and lower surfaces: Close to 138A.

Flower description:

*Flower arrangement, shape and habit.*—Single rotate flowers, flowers usually terminal; flowers face upright and outwardly; freely flowering habit, about seven to nine flowers per lateral branch.

*Fragrance.*—None detected.

*Natural flowering season.*—Long flowering period, plants flower from June through September in Grand Haven, Mich.

*Flower longevity on the plant.*—Last about one week; flowers not persistent.

*Flower buds.*—Length: About 5 mm. Diameter: About 7 mm. Shape: Broadly elliptical. Color: Close to 152B.

*Flowers.*—Diameter: About 3.8 cm. Depth (height): About 1 cm.

*Petals.*—Arrangement: Five in a single whorl. Length: About 1.5 cm. Width: About 1.7 cm. Shape: Rounded to broadly elliptical. Apex: Obtuse. Base: Attenuate. Margin: Entire. Texture, upper and lower surfaces: Smooth, glabrous. Color: When opening, upper surface: Close to 14A. When opening, lower surface: Close to 13A. Fully opened, upper surface: Close to 14A. Fully opened, lower surface: Close to 14B.

*Sepals.*—Arrangement: Ten in two whorls. Length: About 6 mm to 10 mm. Width: About 3 mm to 5 mm. Shape: Ovate or oblanceolate. Apex: Acute. Base: Cuneate or fused. Margin: Entire. Texture, upper and lower surfaces: Smooth, glabrous. Color, upper and lower surfaces: Close to 51A or 152B.

*Peduncles.*—Strength: Strong, flexible. Length: About 8 mm. Diameter: Less than 1 mm. Aspect: Erect to about 30° from vertical. Texture: Smooth, glabrous. Color: Close to 144B.

*Reproductive organs.*—Stamens: Quantity per flower: About 20. Anther size: About 1 mm by 1 mm. Anther shape: Rounded. Anther color: Close to 17B. Pollen amount: Scarce. Pollen color: Close to 17B. Pistils: Quantity per flower: Numerous. Pistil length: Less than 1 mm. Stigma color: Close to 151A. Style length: About 1 mm. Style color: Close to 151A. Ovary color: Close to 139D. Seeds: Length: Less than 1 mm. Diameter: Less than 1 mm. Color: Brown.

Garden performance: Plants of the new *Potentilla* have been observed to have good garden performance and to be tolerant to wind, rain and temperatures ranging from about −35° C. to about 33° C.

Pathogen/pest resistance: Plants of the new *Potentilla* have been observed to be resistant to mildew. Plants of the new *Potentilla* have not been observed to be resistant to pests and other pathogens common to *Potentilla* plants.

It is claimed:

1. A new and distinct *Potentilla* plant named 'Lundy' as illustrated and described.

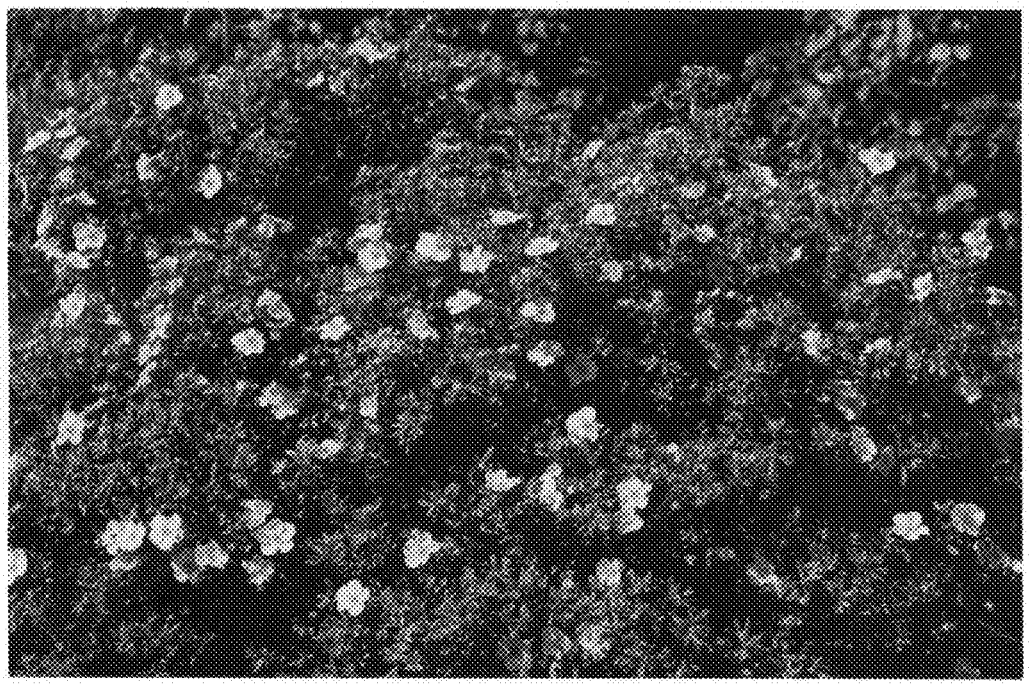

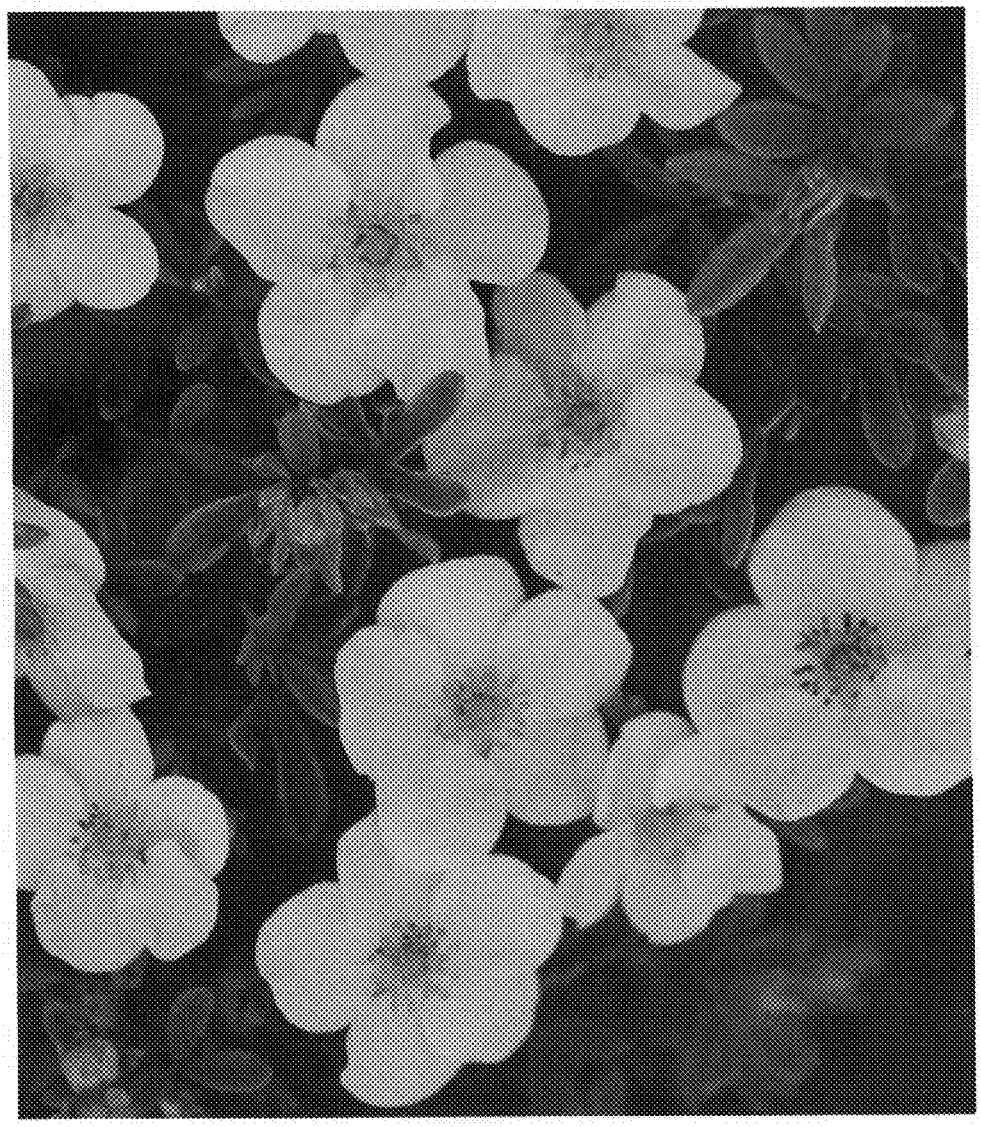

* * * * *